United States Patent [19]

Strauss

[11] Patent Number: 4,907,595
[45] Date of Patent: Mar. 13, 1990

[54] APPARATUS FOR SIMULTANEOUS DETERMINATION OF OPHTHALMIC ARTERY BLOOD PRESSURE AND FLOW

[76] Inventor: Andreas L. Strauss, Aggertalklinik, D-5250 Engelskirchen, Fed. Rep. of Germany

[21] Appl. No.: 95,345

[22] Filed: Sep. 10, 1987

[30] Foreign Application Priority Data

Jan. 10, 1986 [FR] France .................... 86 00257

[51] Int. Cl.⁴ ................................ A61B 5/02
[52] U.S. Cl. ..................... 128/661.06; 128/661.07; 128/691; 128/676
[58] Field of Search .......... 128/672, 677–678, 128/676, 645, 650–651, 661.06–661.08, 662.04, 691, 97.1

[56] References Cited

U.S. PATENT DOCUMENTS

| | | | |
|---|---|---|---|
| 3,308,810 | 3/1967 | Galin | 128/676 |
| 3,371,660 | 3/1968 | Carlin | 128/661.06 |
| 3,453,998 | 7/1969 | Giglio | 128/661.06 |
| 3,605,723 | 9/1971 | King et al. | 128/661.07 X |
| 3,640,270 | 2/1972 | Hoffmann . | |
| 3,835,836 | 9/1974 | Kanter et al. | 128/676 |
| 3,903,871 | 9/1975 | Chisum et al. | 128/676 |
| 3,929,124 | 12/1975 | Yablonski et al. | 128/676 |
| 3,948,248 | 4/1976 | Zuckerman et al. | 128/676 X |
| 4,248,215 | 2/1981 | Bleakley | 128/97.1 X |
| 4,282,882 | 8/1981 | Langham | 128/676 |
| 4,538,618 | 9/1985 | Rosenberg et al. | 128/662.04 |

Primary Examiner—Angela D. Sykes
Attorney, Agent, or Firm—Wegner & Bretschneider

[57] ABSTRACT

The apparatus comprises a chamber (1) enclosed on all sides except for an opening (3) on one side to permit hermetical contact with the orbital borders. The chamber is equipped with a device (4) for increasing the pressure within the chamber, coupled to a manometer (6) and has a doppler probe (5) that may be connected to a doppler flowmeter. Applying an increasing positive pressure in the chamber, and thus upon the contents of the orbit, the doppler probe detects the moment of disappearance and reappearance of the blood flow signal, respectively. The point at which the signal ceases or first reappears corresponds to the systolic blood pressure in the ophthalmic artery.

9 Claims, 1 Drawing Sheet

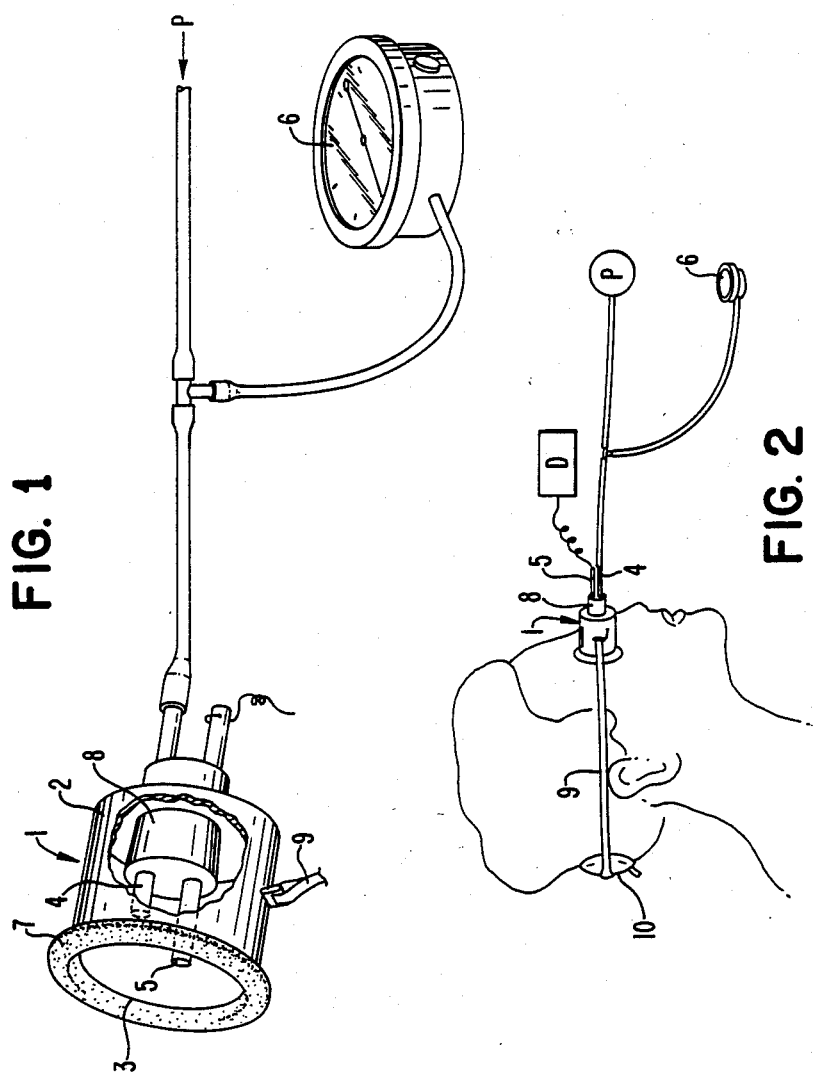

APPARATUS FOR SIMULTANEOUS DETERMINATION OF OPHTHALMIC ARTERY BLOOD PRESSURE AND FLOW

REFERENCE TO RELATED APPLICATION

This application is based on international application PCT/EP87/00009, filed January 9, 1987.

TECHNICAL FIELD

The object of the present invention is a novel apparatus for ophthalmic artery blood pressure (OAP) and flow determination.

BACKGROUND ART

Ophthalmodynamometry (Bailliart, P., Ann.Ocul. 154: 648, 1917) was the first technique developed to determine noninvasively ophthalmic artery pressure by applying a compression on the ocular globe and by visualizing the cessation and beginning of the central retinal artery pulsations, respectively. This technique gave rise to developments of further OAP measurement procedures such as the ophthalmodynamography of Hager (Hager, Klin. Mbl. Augenheilkunde 141, 801–840, 1962) and the ocular pneumoplethysmography of Gee (Gee et al., Med. Instrum. 8, 244, 1974).

Ophthalmodynamometry gives rise to major inherent inaccuracies and technical difficulties including non-transmitted vectors of compression, movements of the globe during visualisation of the nerve head, subjectivity of the ophthalmoscopic observation of the central retinal artery pulsations and unpracticability in case of opacification of one of the refracting eye structures (Galin et al., Am. J. Ophthalmol. 67, 388, 1969).

The ophthalmodynamography of Hager, utilizing a pressure transducer in an orbital chamber, causes potential technical errors related to pressure-volume interactions with signal distortion during unvoluntary eye movements of the patients and muscle twitches and presents low correlation with systemic blood pressure (Sayegh, F., p. 163–167, in: Finke, J.(ed): Ophthalmodynamographie, Stuttgart, Schattauer Verlag, 1974).

The ocular pneumoplethysmography uses vacuum deformation of the globe by application of a vacuum of 300 to 500 mm Hg (40 to 66 KPa, resp.) upon the eye in order to rise intraocular pressure. This procedure causes subconjunctival hemorrhage and requires the instillation of local anesthetics. Furthermore, as interocular pressure cannot be directly measured, it has to be derived from calibration tables relating the applied force (negative pressure) to the value of produced intraocular pressure measured in animal experiments. This relationship is a nonlinear one and strongly dependent on the size of the eyeball that is furthermore liable to change during life time (Gee,W., Surv. Ophthalmol. 29,276, 1985). Finally, none of these methods can provide information on flow parameters.

SUMMARY OF THE INVENTION

The inventor has now originally developed a new device, named Ophthalmomanometry-Doppler (OMD), that informs simultaneously about both perfusion pressure and flow direction in the ophthalmic artery. This technique is a noninvasive, simple and rapid method that does not require any pharmaceutic application and presents no disadvantages for the patient.

The object of the present invention is an apparatus for measurement of the ophthalmic arterial blood pressure and flow which comprises: (a) a rigid chamber enclosed on all sides except for an opening on one side to permit intimate contact with the orbital borders or their neighbouring parts; (b) means to increase the pressure within the chamber up to the point where blood flow in the ophthalmic artery ceases while the chamber is in place on the orbital borders; (c) a manometer connected to the said chamber to permit measurement of the pressure within said chamber and (d) a doppler probe that may be positioned on the periorbital ophthalmic branches to detect the disappearance and reappearance of the doppler signal. The doppler probe is connected to a standard continous wave or pulsed Doppler flowmeter. The means for increasing the pressure within the chamber may comprise an arrival pipe for compressed air that is coupled to the manometer, the arrival of the compressed air occurs either automatically or by manual inflation. The doppler probe can be either a button transducer fixable directly on the skin or a pencil transducer mounted on a flexible spring suspension that ensures continuous contact to the skin.

In order to facilitate the positioning of the doppler probe over the periorbital ophthalmic branches, the walls of the OMD-chamber may be transparent or equipped with a transparent window. For instance, the chamber may be made of a plastic material such as plexiglass, polyvinyl acetate, etc., or of glass. According to the invention, the adaptability of the OMD to the orbital borders must be such that the chamber, applied upon the orbit, has to close hermetically when a positive pressure up to 170 mm Hg (22 KPa) is set inside in order to compress the artery. Consequently, the opening of the chamber may advantageously be surrounded by an elastic gasket, for example of a silicon leaf, in order to eliminate air leaking at the skin level during the measurement procedure. Several sets of easily exchangable orbital gaskets may be developed for different orbital sizes and forms as well as for disinfection purposes.

According to the invention, the OMD-chamber can be either fixed and held manually by an assistant upon the orbital borders of fastened with a belt behind the head. In this latter case, the belt can be tightened in order to ensure a hermetical closure of the chamber upon the orbit. Furthermore, the belt can be equipped behind the head with an air-cushion. During the measurement procedure, the inflation of this air cushion exerts a supplementary traction of the OMD-chamber against the orbital borders in order to neutralize (counteract) the detaching force component of the positive chamber pressure. The inflation of the OMD-chamber and of the air cushion can occur simultaneously from the same compressed air arrival tube or from two different sources.

According to another feature, the arrival pipe for compressed air and the doppler probe are arranged within one component which is separable from the chamber. Such an arrangement may be advantageous for replacement or disinfection purposes.

BRIEF DESCRIPTION OF THE DRAWINGS

The invention is now described in more details in reference to the drawings where FIG. 1 is a perspective representation of a realisation of the OMD-apparatus and FIG. 2 is a schematic representation of the device in place over the patient's orbita in measurement position.

BEST MODE FOR CARRYING OUT THE INVENTION

The OMD-apparatus consists in a cylinder-like chamber 1 with rigid and possibly transparent walls 2, enclosed on all sides except for an opening 3. The opening 3 has an oval shape and is surrounded by an orbital elastic gasket 7 hermetically adaptable to the form of the outer orbital borders or their neighbouring parts. This gasket is easily exchangable for spare ones in order to fit perfectly to different orbital sizes. Opposite to the opening 3, the chamber is hermetically closed and equipment with an arrival pipe 4 for compressed air from a device P and a doppler probe 5. Both the arrival pipe 4 and the doppler probe 5 may be arranged within one component 8 which can be detached from the chamber 1. The arrival pipe 4 for compressed air is connected to a manometer 6 with graduations in particular between 0 and 200 mm Hg (0 and 26 KPa). The doppler probe 5 that can be a button or pencil transducer, is connected to a commercial medical doppler flowmeter D. Both the doppler transducer and flowmeter can be either of continuous wave or of range-gated pulsed doppler system. Both doppler systems are commercially available and used in the diagnosis of the arterial disease. The chamber walls have chucks for belt 9 fixation. The belt 9 contains behind the head an air cushion 10 (FIG. 2) in order to pull the chamber 1 during the measurement procedure tighter against the orbital borders.

The measurement procedure consists in applying the OMD-chamber to the orbital borders and in tightening the belt in order to achieve a hermetical closure. The Doppler probe is coupled with an acoustic gel to the skin of the medial angle of the closed lid. The transducer is positioned over the medial frontal artery and angled to achieve the strongest doppler signal. After recording the velocity wave form in order to establish the flow direction in the frontal artery, a positive pressure is applied within the chamber and transmitted to the orbital contents while the doppler transducer continues detecting frontal arterial Doppler shift. The pressure within the chamber when the audio doppler signal completely ceases while increasing the pressure, or first reappears while reducing the pressure, indicates the systolic pressure in the ophthalmic artery. This measured ophthalmic artery pressure reflects the systolic pressure in the intracranial internal carotid artery which first major branch is the ophthalmic artery.

The major terminal branches of the ophthalmic artery anastomose freely with several branches of the external carotid artery. Under normal conditions, as the pressure within the internal carotid artery exceeds that in the terminal branches of the external carotid artery, flow within the branches of the ophthalmic artery is outward or antegrade toward the arteries of the face. In case of an occlusive internal carotid arterial disease the pressure in the internal carotid as well as ophthalmic artery is diminished. The level of pressure reduction depends mainly on the collateral blood supply from the Circle of Wilis. The OMD-device detects this reduction in the ophthalmic arterial pressure (OAP). When this OAP is related to the systemic or brachial artery pressure (BAP) the OAP/BAP ratio is diminished. The OAP/BAP ratios for healthy normotensive volunteers free from cerebrovascular disease mesured with the present OMD-apparatus range from 0.60 to 0.77 with a mean (+SD) of 0.68+0.04 (n=60 healthy volunteers). In patients with occlusive extracranial carotid arterial disease and with an inadequate collateral blood supply, this OAP/BAP ratio, measured with the present OMD-apparatus, is below 0.60 with a mean (+SD) of 0.42+0.03.(n=12 patients).

I claim:

1. An apparatus for measurement of ophthalmic arterial blood pressure and flow which comprises (a) a rigid chamber means enclosed on all sides by walls except for an opening on one side for intimately contacting the orbital border or their neighboring parts around the eye cavity; (b) means for increasing the pressure within said chamber means when the chamber means is applied on the orbital borders to the point where blood circulation through the ophthalmic artery ceases; (c) a manometer connected to said chamber means to permit measurement of the pressure within said chamber means; and (d) a Doppler probe means within the chamber means for positioning on the periorbital ophthalmic branches to detect the point when blood flow ceases or reappears, respectively.

2. An apparatus according to claim 1, wherein the walls of the chamber means are transparent.

3. An apparatus according to claim 1, wherein the walls of the chamber means are equipped with a transparent window.

4. An apparatus according to claim 1 wherein said means for increasing the pressure within the chamber means comprises an arrival pipe for compressed air.

5. An apparatus according to claim 4, wherein the arrival pipe for compressed air and the Doppler probe means are arranged within one component which is separable from the chamber means.

6. An apparatus according to claim 1, which further comprises means for maintaining the apparatus in position on the head of a subject being tested with the apparatus, the means for maintaining comprising a belt attached to the chamber means.

7. An apparatus according to claim 6, wherein the belt is provided with an air cushion for engaging the back of the head of the subject.

8. An apparatus according to claim 1, further comprising means for forming a hermetic seal surrounding the opening.

9. An apparatus according to claim 8, wherein said means for forming a hermetic seal comprises an elastic gasket.

* * * * *